US008062282B2

(12) United States Patent
Kolb (10) Patent No.: US 8,062,282 B2
(45) Date of Patent: Nov. 22, 2011

(54) METHODS AND APPARATUS FOR TEMPORARILY OCCLUDING BODY OPENINGS

(75) Inventor: Gloria R. Kolb, Milton, MA (US)

(73) Assignee: Fossa Medical, Inc., Sandy Hook, CT (US)

( * ) Notice: Subject to any disclaimer, the term of this patent is extended or adjusted under 35 U.S.C. 154(b) by 0 days.

(21) Appl. No.: 11/673,301

(22) Filed: Feb. 9, 2007

(65) Prior Publication Data

US 2007/0191768 A1   Aug. 16, 2007

Related U.S. Application Data

(60) Provisional application No. 60/772,797, filed on Feb. 13, 2006.

(51) Int. Cl.
*A61M 31/00* (2006.01)

(52) U.S. Cl. .......................................... 604/514; 604/61

(58) Field of Classification Search ................... 604/41, 604/60, 84, 85, 265, 288, 514, 61
See application file for complete search history.

(56) References Cited

U.S. PATENT DOCUMENTS

| | | | |
|---|---|---|---|
| 5,071,644 A | 12/1991 | Viegas | |
| 5,277,911 A | 1/1994 | Viegas | |
| 5,292,516 A | 3/1994 | Viegas | |
| 5,298,260 A | 3/1994 | Viegas | |
| 5,300,295 A | 4/1994 | Viegas | |
| 5,306,501 A | 4/1994 | Viegas | |
| 5,318,780 A | 6/1994 | Viegas | |
| 5,346,703 A | 9/1994 | Viegas | |
| 5,366,735 A | 11/1994 | Henry | |
| 5,407,445 A | 4/1995 | Tautvydas | |
| 5,800,711 A | 9/1998 | Reeve | |
| 5,843,470 A | 12/1998 | Reeve | |
| 5,958,443 A | 9/1999 | Viegas | |
| 6,152,943 A * | 11/2000 | Sawhney | 606/193 |
| 6,346,272 B1 | 2/2002 | Viegas | |
| 6,399,624 B1 | 6/2002 | Reeve | |
| 6,436,425 B1 | 8/2002 | Henry | |
| 6,475,182 B1 * | 11/2002 | Hnojewyj et al. | 604/82 |

(Continued)

FOREIGN PATENT DOCUMENTS

CA            2040460            6/1997

(Continued)

OTHER PUBLICATIONS

Properties of Pluronic F-127 http://worldaccount.basf.com/wa/NAFTA~en_US/Catalog/ChemicalsNAFTA/pi/BASF/Brand/pluronic.*

*Primary Examiner* — Kevin C Sirmons
*Assistant Examiner* — Bradley Osinski (57) ABSTRACT

Methods and apparatus are provided for temporarily occluding a body lumen. A method in accordance with one or more embodiments of the invention includes introducing a tip of a catheter into the body lumen, the tip including a central longitudinal axis; expelling a thermosensitive polymer from the tip of the catheter into a portion of the body lumen, with at least a portion of the thermosensitive polymer being expelled from the tip in a direction generally radially outward from the central longitudinal axis to improve adherence of the thermosensitive polymer to a wall defining the body lumen; and at least partially withdrawing the tip from the body lumen and allowing the thermosensitive polymer to harden as it warms to body temperature to form a plug in the body lumen.

24 Claims, 5 Drawing Sheets

U.S. PATENT DOCUMENTS

| | | |
|---|---|---|
| 6,544,227 B2 | 4/2003 | Sahatjian |
| 6,565,530 B2 | 5/2003 | Sahatjian |
| 6,663,594 B2 | 12/2003 | Sahatjian |
| 6,761,824 B2 | 7/2004 | Reeve |
| 6,840,899 B2 * | 1/2005 | Koga et al. ............... 600/29 |
| 6,977,045 B2 | 12/2005 | Reeve |
| 2003/0109587 A1 * | 6/2003 | Mori ............... 514/772.3 |
| 2003/0199654 A1 | 10/2003 | Zhang |
| 2003/0215519 A1 | 11/2003 | Schwarz |
| 2004/0024136 A1 | 2/2004 | Zhang |
| 2004/0197264 A1 | 10/2004 | Schwarz |
| 2004/0224021 A1 * | 11/2004 | Omidian et al. ............... 424/484 |
| 2005/0008610 A1 | 1/2005 | Schwarz |
| 2005/0113285 A1 | 5/2005 | Zhang |
| 2005/0143678 A1 | 6/2005 | Schwarz |
| 2005/0147585 A1 | 7/2005 | Schwarz |
| 2006/0269512 A1 | 11/2006 | McDougal |

FOREIGN PATENT DOCUMENTS

| | | |
|---|---|---|
| CA | 2316248 | 7/1999 |
| CA | 2044878 | 12/2000 |

* cited by examiner

METHODS AND APPARATUS FOR TEMPORARILY OCCLUDING BODY OPENINGS

RELATED APPLICATION

The present application claims the benefit of U.S. Provisional Patent Application No. 60/772,797 filed on Feb. 13, 2006 and entitled "Methods and Devices for Temporarily Occluding Body Lumens," the disclosure of which is incorporated herein by reference in its entirety.

BACKGROUND OF THE INVENTION

The present application relates generally to medical devices and, more particularly, to medical devices for temporarily occluding body lumens.

Medical devices are often used to facilitate the flow of material as, e.g., in a ureteral stent used for drainage of urine from the kidney to the bladder, or in a vascular graft used to maintain blood flow. However, there are times when it would be preferable to stop flow or occlude a lumen temporarily such as, e.g., to block blood flow until a clot has formed, to block a bodily fluid until a surgery is complete, to block a passageway to protect another part of the body, to block the urethra to prevent urinary leakage or bleeding, to block the fallopian tube or vas deferens to prevent conception, or to block a passageway to compartmentalize pressure or material to one part of the lumen and not another. In many of these cases occlusion is only needed temporarily.

Current occlusion devices, backstops or plugs are often difficult to place, difficult to maintain in position, can be potentially traumatic, and need removal physically to be temporary. Placement of a physical solid plug or similar device may not create sufficient obstruction of the body passageway depending on the nature of the occlusive device. For example, the occlusive device may be incorrectly sized and too small to create complete obstruction, and may be incorrectly shaped for complete occlusion, or be slightly permeable. An occlusive device placed in the fallopian tubes, e.g., might be too small to securely seal against the fallopian tube walls or might be formed of a screen like structure and thus be slightly permeable. It might create an obstruction sufficient to prevent the passage of an egg past the occlusive device, but might in fact be dangerous if sperm, a much smaller cell than the egg, is able to pass the obstruction and fertilize the egg upstream of the obstruction, creating an ectopic pregnancy.

Placement of an occlusive device with a predefined shape may not conform to the lumen, resulting in incomplete obstruction. For example, ureters are not cylindrical, but have irregular cross-sections with multiple folds. A tubular or spherical device, even one that expands may not occlude these folds. Additionally, even if the occlusive device is shaped to fill the entire lumen, fallopian tubes tend to recannalize around an obstruction. Similarly, ureters and vascular lumen can dilate around the occlusive device and thereby resist obstruction.

One method addresses this problem by enhancing tissue ingrowth into the device. However, this may not be practical if the occlusion is to be temporary. Another method is to externally apply pressure to the intended area. For example, in vascular lumens, this method attempts to block flow from the vein or artery until the natural clotting process is complete. Pressure may be manually applied with, e.g., a staple, clip, or clamp. However, this method may damage internal or external tissue and is only viable if access to the lumen is available externally.

Another method addresses temporarily occluding a lumen by using a balloon. Balloons can withstand high pressure. It may be difficult to control the pressure, which can result in overpressurizing or overdilating the balloon, leading to injured tissue. For example, the inflated arterio balloon dilates the artery, potentially injuring the intima, which can lead to thickening and narrowing of the artery.

For patients with urinary fistulas, diversion of urine is performed by a percutaneous transrenal approach with ureteral occlusion. Ureteral occlusion previously was obtained by detachable and non detachable balloons, but migration as well as deflation of the balloons occurred relatively frequently, leading to recurrence of the urine leakage. A silicone ureteral occluder was developed and used with only limited success because of device migration and incomplete ureteral occlusion. It appears that the best results have been accomplished with Gianturco coils and Gelfoam embolization. Even with multiple coil placements, together with Gelfoam plugs, the ureteral occlusion is sometimes achieved for only weeks or months, and was attributed mostly to the induced urothelial hyperplasia. Coil migration was frequently encountered. The lack of an appropriate self-anchoring mechanism results in coil migration, which eventually deteriorates the occlusive effect.

Another method of internally occluding blood vessels is a "T" shaped device with a bulbous tip placed at either end of the "T." These devices are manufactured from silicon rubber. The bulbous tips of the device are inserted into each of the two parts of the vessel. The bulbous tips have to be correctly sized to effectively occlude the blood vessel. In clinical practice, these devices reduce bleeding at the arteriotomy, but do not stop bleeding.

Percutaneous occlusion techniques have become important tools in minimally invasive management of a wide range of pathological conditions. Use of permanent mechanical occlusion devices, such as coil embolization, has been shown equivalent to that of surgical ligation. The Gianturco-Wallace stainless steel coil (Cook Inc., Bloomington, Ind.) has been a widely used permanent, expandable intravascular occlusion device for transcatheter delivery. The coil and other mechanical occlusion devices have a number of drawbacks, the largest one being that they are typically permanent or implanted, which is undesirable for certain applications.

Other temporary backstops, such as the NTrap (Cook Urological) or Stone Cone (Boston Scientific), are designed to allow certain size fragments to pass through in the ureter. However, in addition to these devices not fully occluding (which may be desirable in certain clinical circumstances), these devices need to be restrained by a wire, tether or the like for retrieval. The restraint may get in the way of other procedures such as laser lithotripsy. The restraint may become detached and additional procedures may be required to retrieve the unconstrained segment of the backstop.

Other device occlusion concerns in body lumens are high flow conditions. A coil anchoring system has been devised for vascular application, however often rendering the system non-repositionable or removable. Additional concerns with existing occlusion devices are the need for specialized equipment, the time required for installation and the complexity of the procedure, all resulting in greater cost to the patient.

BRIEF SUMMARY OF EMBODIMENTS OF THE INVENTION

Methods and apparatus are provided for temporarily occluding a body lumen. A method in accordance with one or more embodiments of the invention includes introducing a tip of a catheter into the body lumen, the tip including a central longitudinal axis; expelling a thermosensitive polymer from the tip of the catheter into a portion of the body lumen, with at least a portion of the thermosensitive polymer being expelled from the tip in a direction generally radially outward from the central longitudinal axis to improve adherence of the thermosensitive polymer to a wall defining the body lumen; and at least partially withdrawing the tip from the body lumen and allowing the thermosensitive polymer to harden as it warms to body temperature to form a plug in the body lumen.

An apparatus for temporarily occluding a body lumen in accordance with one or more embodiments of the invention includes a catheter including a tip at one end thereof, the tip being insertable into the body lumen, the tip including a central longitudinal axis; and a mechanism connected to the catheter and operable by a user for expelling a thermosensitive polymer from the tip of the catheter into a portion of the body lumen; wherein the tip includes one or more openings at a side thereof to allow at least a portion of the thermosensitive polymer to be expelled from the tip in a generally radially outward direction from the central longitudinal axis to improve adherence of the thermosensitive polymer to a wall defining the body lumen, the thermosensitive polymer capable of hardening as it warms to body temperature to form a plug in the body lumen.

Various embodiments of the invention are provided in the following detailed description. As will be realized, the invention is capable of other and different embodiments, and its several details may be capable of modifications in various respects, all without departing from the invention. Accordingly, the drawings and description are to be regarded as illustrative in nature and not in a restrictive or limiting sense, with the scope of the application being indicated in the claims.

BRIEF DESCRIPTION OF THE DRAWINGS

FIGS. 18-21B are perspective views of various catheter tips with side openings in accordance with one or more embodiments of the invention.

DESCRIPTION OF THE PREFERRED EMBODIMENTS

In accordance with one or more embodiments of the invention, methods and devices are provided for temporarily occluding body lumens by providing a moldable, dissolvable plug (described as gel or plug) within the body lumen. This system may be inserted using generally minimally invasive techniques, be left in long enough to serve its function and then be simply removed or dissolved.

In one or more embodiments, the dissolvable plug is in the form of a semi-solid material or gel. The gel may be viscous, adhering to the lumen lining and filling the variance in size. The gel may be in the form of a capsule (as described, e.g., in further detail below with respect FIGS. 3A and 3B), wherein the thin membrane of the capsule is readily dissolvable by fluid contact or obtaining body temperature. Alternatively, the gel may come in a hardened preformed shape of the lumen and then softened to flow and fill the intended area. The gel may start off as a liquid and become more viscous as it changes temperature.

In one or more embodiments, the gel is placed to fill a framework or scaffolding to better hold its shape as described, e.g., in further detail below with respect to FIGS. 4A and 4B. The scaffolding may first gently dilate the lumen radially to better wedge and take hold under pressure. The scaffolding may include expandable wire links, fence, screen, or similar material that presses around the perimeter of the lumen to dilate or may stretch across the cross-sectional area. The scaffolding may be made of plastic or metal, possibly with memory such as nitinol, and physically removed, or be made of a different composition of gel, polymer, or other dissolvable or bioabsorbable material that diminishes.

In one or more embodiments, the gel may contain drugs for localized delivery. For example, the gel may contain heparin or other drugs to reduce thrombogenic tendencies in a vascular lumen. In one or more embodiments, the gel contains pain killers such as lidocaine. In one or more embodiments, the gel contains alpha-blockers or other drugs to relax the muscle tissue, which is particularly useful in the ureter. In one or more embodiments, the drug promotes hemostasis. In one or more embodiments, the gel contains a sclerosing agent, whose application could be useful to close up varicose veins or arteries feeding blood to tumors. In one or more embodiments, the gel contains growth factors or medications for tissue healing, which promote repair and regrowth of damaged or incised normal tissues.

In one or more embodiments, the gel can quickly dissolve from the center of the plug radially out to the lining, with the dissolved substance flowing downstream to provide a protective lining within the lumen. For example, in a thermosensitive polymer, the center can be cooled using a cold probe or water jet to liquefy the material, which runs down the body lining hardening again when in contact with the wall lining downstream. In one or more embodiments, it may be advantageous for the gel to dissolve around the perimeter, or near the lumen wall first, to dislodge the plug from the wall intact. For example, the plug may be released from the ureter wall and the entire cluster may push debris, fragments, clots or other obstacles down the lumen.

In one or more embodiments, the application of the gel allows for a method of pressurizing one compartment of the passageway as further described below, e.g., with respect to FIG. 6. For example, the gel plug could allow for pressurizing the ureter and bladder for easy visualization with a scope while the wall folds open up, but protect the kidney from too much pressure.

In one or more embodiments, the plug can prevent particles or materials from going to another part of the body. For example, when a percutaneous nephrolithotomy procedure is performed, a plug at the ureteropelvic junction code can help contain the particles for removal with the percutaneous instruments. Similarly, a plug in the ureter could help contain particles, fragments, and stones from traversing up the ureter into the kidney. In one or more embodiments, the plug can be used to contain particles or materials for capture, such as in a fallopian tube to harvest eggs.

In one or more embodiments, the gel is used to transiently seal leakage around tubes such as a suprapubic drainage tubes, percutaneous nephrostomy tubes, or after a percutaneous nephrolithotomy procedure. In one or more embodiments, the gel is used to transiently stop urine flow from upper tract to bladder, e.g., when there is hematuria. This is done in conjunction with a percutaneous nephrostomy tube. In one or more embodiments, the gel serves as a coagulum to trap particles such as stone particles or dust for more complete extraction. In one or more embodiments, the gel is used to prevent travel in an opposite directions, e.g., to prevent reflux during installation of chemotherapeutic or sclerosing agents such as Formalin.

In one or more embodiments, the purpose of the plug may be served in a few minutes to a few hours. In other embodiments, the plug is used for longer periods of time. For example, the plug may be applied to the fallopian tube or vas deferens to prevent conception, where the temporary timeframe may be months or even years. In some cases, the plug should not stay in place in a body lumen beyond a certain length of time such as, e.g., ten minutes in a vascular system. It may be more important in these cases for the plug to be very solid and secure to be able to withstand high blood flow pressure.

The plug in accordance with one or more embodiments is useful for the above-mentioned uses in the ureter, vascular system, urethra, fallopian tube and vas deferens. The plug is also be useful for other uses, e.g., in the biliary system to prevent stones from falling into the common bile duct during gallbladder removal, in the urethra for prostate surgery, in pediatrics for hard to reach areas, and in many other areas where a temporary plug may be useful such as, e.g., the nasal passageway, breast duct, colon, digestive system, esophagus, central nervous system, etc.

There is a need to efficiently deliver the plug to the intended area, particularly in structures with a small lumen. In one or more embodiments of the invention, a catheter is used to deliver the plug in a less viscous state, such as in a liquid state. The catheter material is flexible and can include an insulator material such as, e.g., polyimide, polyolefin, polyether block amides, and polyester. The insulation helps reduce the possibility of the plug significantly hardening before complete delivery. In many uses, the plug would need to travel in a narrow, but very long passageway, which can become difficult as the laminar flow is reduced. For example, a typical ureteroscope, wherein a catheter may deliver a plug to the ureter, is about 70 cm long, yet has an inner diameter of only about 1 mm.

In one or more embodiments, the gel is pre-inserted into the tip or distal region of the catheter, so it does not need to traverse the entire length of the catheter. The plug can then be left in a more viscous state. In one or more embodiments, the gel is sucked into the catheter first to be held within the distal region. The viscosity of the gel material itself may be enough to be contained within the catheter itself. In one or more embodiments, the delivery system has an endcap or protective film covering the gel material that is removed prior to use. In one or more embodiments, the catheter tip is tapered slightly to a smaller diameter to reduce premature leakage. In one or more embodiments, the catheter has a flexible rubber or silicone-like end with one or more slits that open upon force or pressure. In one or more embodiments, the rubber or silicone-like end is a flap attached in one section that opens with force. In one or more embodiments, the opening or multiple openings with or without slits, caps, flaps, etc is on the side of the catheter tip, with the catheter axial end closed. The side opening would allow the gel material to be forced radially to the lumen wall instead of down the lumen axis. In cases where one side port was available, the catheter could spin to fully apply the plug material to the sides. In one or more embodiments, the flap or cap is dissolvable or bioabsorbable. In one or more embodiments, the entire distal end is the gelatinous material itself.

In one or more embodiments, the gel material is pushed out of the tip either by air pressure, liquid pressure, or by a physical plunger that is activated by a mechanism by hand outside of the body. For example, a standard syringe plunger may be sufficient. In one or more embodiments, a tether attached to the distal end is pulled to physically release or squeeze out the material. In one or more embodiments, a more sophisticated hand lever can be used to provide more power to the pushing or pulling mechanism.

In one or more embodiments, the gel is formed from two separate components, e.g., two liquid parts, or a solid and a liquid part, which are then mixed or activated at the tip of the catheter. In one or more embodiments, a fractionated polymer is preassembled as a fine powder form in the tip of the catheter. Water or other liquid is then inserted into the catheter at time of delivery, and travels the length of the catheter to wet the powder to form the gel material. In one or more embodiments, a powder or other substance forms a gel when it comes into contact with a body fluid. In one or more embodiments, two liquids travel in a multi-lumen catheter where the separating wall is removed in the tip for the two liquids to mix to form the gel material as described in further detail below, e.g., with respect to FIGS. 15 and 16. In one or more embodiments, the two materials travel through a turbulent pathway at the tip to enhance the mixing.

In one or more embodiments, the plug is delivered as a solid, hard gel that then softens with body temperature and fills the body lumen or cavity. In one or more embodiments, a soft or liquid plug is inserted like a capsule, within a coating or lining. The coating or lining dissolves in the fluid, thereby releasing the plug that then conforms to the body shape and hardens with temperature. The above mentioned coating or lining could also be bioabsorbable.

In one or more embodiments, a tether that is attached to the distal end may be pulled to physically flatten the gel material axially, allowing the gel to radially expand and conform to the lumen as described in further detail below, e.g., with respect to FIGS. 17A and 17B.

In one or more embodiments, the plug within its containment structure is liquefied first by surrounding it with a cold pack or cold or ice water. This temporarily lowers the plug temperature to be deliverable, and/or formable to the body, before it heats up to body temperature and hardens.

There is a need for simple, atraumatic removal system of the plug. In a thermosensitive gel material, a cold material can be applied to the gel to liquefy it. In one or more embodiments, cold water or other cold liquid is deployed or distributed onto the surface of the gel. In one or more embodiments, the water is deployed inside the gel material by first poking the surface with the delivery catheter or hollow wire. The liquid delivery system could be the same one that is used to deliver the gel material. The cold liquid could also be formed by the same cold pack used around the gel delivery system. The wire could also be a guidewire and is sufficiently stiff to poke through a viscous material. In one or more embodiments, the removal of the gel is by liquification from a cold metal probe such as a cryo-probe. In another thermosensitive gel material, the opposite is true and a hot material or liquid is applied to liquefy it.

In one or more embodiments, the gel material is simply diluted by the bodily fluid or external liquid. In one or more embodiments, the gel material is hollowed out and scraped to reduce the material sufficiently for the dissolving or diluting process to begin.

In one or more embodiments, cooling channels in the catheter are used with a gas or liquid to cool the material down before delivery, and/or used to remove the material. Alternatively, a cold metal or cryo-probe may be placed inside the catheter to exit at the distal end only where it is needed.

The gel may be made of a natural gelatin, such as pharmaceutical-grade bone gelatin, or a synthetic polyol or thermosensitive polymer such as a block copolymer. The block copolymer may be composed of polyethylene glycol and polyoxyalkylene block copolymers. Poloxamers may be suitable due to their low toxicity to body tissue wherein the polyethylene blocks are separated by the polyoxypropylene center block. Purified polymers may be even more suitable to narrow the range of molecular weights to reduce the temperature transition time, reduce the side effects from the lower molecular weight molecules and increase the consistency of the transition. Polymers may be purified by a variety of processes, including aqueous two-phase system (U.S. Pat. No. 6,761,824), salt/alcohol extraction system (U.S. Pat. No. 6,977,045), super critical fluid extraction (U.S. Pat. No. 5,567,859), and chromatography.

One example of a suitable thermosensitive polymer is a mixture of Poloxamer 338 (Pluronic® F108 available from BASF) at 10-35% (preferably 25%) and the rest water. The amount of the base material relative to water can be varied depending on the viscosity desired and the desired temperature at which the material begins to harden. The viscosity can be anywhere from 100 cps up to 1,000 kcps (or more) in this example. Other suitable Poloxamers include Poloxamers 407, 237, and 188, which can be used alone or in some combination thereof in a mixture with water.

In a preferred embodiment, the plug has a viscosity of 0.2 kcps or less at room temperature and changes to at least 200 kcps at body temperature. The plug preferably changes within a 5 degree C. temperature differential or less between 25 and 35 degrees C. More likely the plug will be around 0.2 kcps at room temperature. The plug can easily go up to 1200 kcps. The plug is preferably released with 20 or 30 ml of cold water or less, depending on the cavity that was filled.

In one or more embodiments, the gel contains radiopaque material to be seen on x-ray. In one or more embodiments, the gel contains colorants or darkeners to be visualized through a scope.

Figure 1:
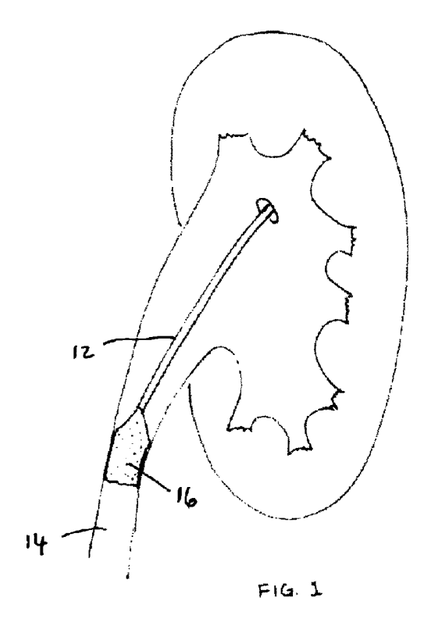
FIG. 1 is a perspective view of a ureter being filled percutaneously with a plug in accordance with one or more embodiments of the invention.

FIG. 1 is a perspective view of a ureter being filled percutaneously with a plug in accordance with one exemplary embodiment of the invention. A gelatinous material is expelled from a delivery device 12 into a body lumen 14 to occlude the lumen 14 and form a plug 16. In this embodiment, the non-solid gel is a thermosensitive material that hardens when heated to body temperature. It is shown delivered to the uretero-pelvic junction percutaneously. In this view, the material is viscous enough to adhere to the wall lining. The delivery device 12 is so sized in diameter to fit inside the created opening or endoscopic instruments.

Figure 2:
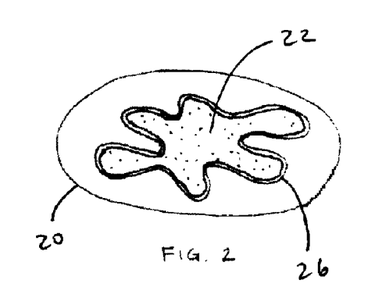
FIG. 2 is a cross-sectional view of a ureter fully occluded with a plug in accordance with one or more embodiments of the invention.

FIG. 2 is a cross sectional view of a ureter 20 filed with the gelatinous material 22 conforming to the varying perimeter of the ureteral wall lining 26. It is apparent that a preformed or rigid plug, most likely of circular cross section, may not adequately fill in all the folds of the ureteral wall lining 26.

Figure 3A:
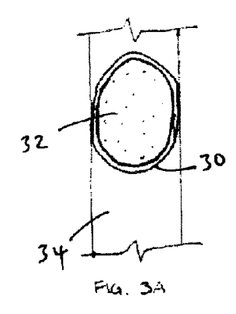
FIGS. 3A and 3B are cross-sectional views of a lumen illustrating the insertion of a capsule in the lumen and its subsequent formation as a plug in accordance with one or more embodiments of the invention.
Figure 3B:
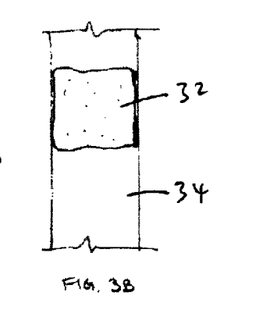

FIG. 3A shows another embodiment of the gel being delivered as a capsule with a hardened outer layer 30, which may be a different material such as a dissolvable pharmaceutical grade bovine gelatin. The capsule 30 surrounds a liquid gel 32. The capsule 30 provides a protective temporary boundary and helps to prevent the gelatinous material from heating up (and therefore hardening) too quickly before full delivery or from diluting too quickly upon delivery to form enough mass to reach or adhere to the lumen wall 34. The capsule 30 may dissolve faster than the gel 32 inside hardens, and so the gel 32 flows to fill the empty gap to the body lining as shown in FIG. 3B before fully reaching body temperature and body temperature viscosity. For example, body temperature viscosity may be ideal around 250 kcps for peanut-butter like consistency in the ureter or around 1200 kcps or more for lard like consistency (at room temperature) inside the fallopian tube. The lower viscosity would be particularly suitable for a quick temperature change needed in a high flow situation, such as blood or urine, and also allow for quick removal after a surgical procedure. The higher viscosity would be more suitable for a more long lasting effect.

Figures 4A, 4B:
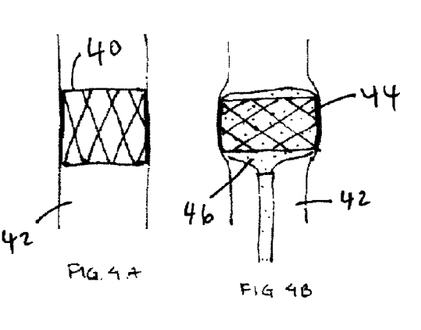
FIGS. 4A and 4B are cross-sectional views of a lumen illustrating use of scaffolds with plugs in accordance with one or more embodiments of the invention.

FIG. 4A shows a scaffolding 40 that can be inserted in a lumen 42 and then filled with gel in accordance with one or more embodiments of the invention. The scaffolding can help give the gel structure before it hardens, to help prevent the gel from traversing down the lumen before fully deployed, as well as to help the gel to adhere to the lumen lining. In this embodiment, the scaffolding is partially expanded radially from a smaller configuration for delivery. In other embodiments, it is fully sized. The scaffolding may be near the wall lining to help the gel adhere to the lumen in that area, or be closer to the center to give the weakest area more strength. The scaffolding may be around the perimeter or fill the structure within.

As shown in FIG. 4B, a scaffolding 44 may be deployed in a lumen 42 such that the lumen is further expanded beyond the lumen diameter, and then the scaffolding 44 is filled with the gel 46. Dilating the lumen slightly can help the plug to stay in place, especially if the body lumen expanded. If the body lumen expanded around the plug, the plug would probably migrate in the direction of fluid flow until it hit non-dilated lumen, thereby reforming the plug. In cases of high flow, such as arterial flow, the flow itself is continually applying pressure on the gel against undilated portions, thereby providing a continuous seal. Certain body lumens may continue to dilate to reestablish flow; however the amount of expansion of the scaffolding would be partially determined so that the time for dilation for the entire length of potential occlusion area is greater than the time needed to accomplish the procedure at hand.

Figure 5:
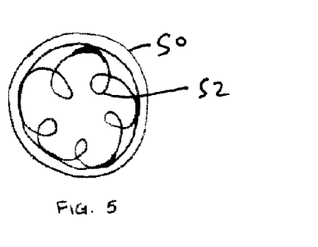
FIG. 5 is a cross-sectional view of a lumen with a scaffold inserted therein in accordance with one or more embodiments of the invention.

FIG. 5 is a cross sectional view of a lumen 50 with a scaffolding 52, where the scaffolding 52 provides support for the inner portion of the lumen 50. The scaffoldings in FIGS. 4A and 4B have a diamond pattern which can be easily expanded and contracted radially. However, many different patterns can be used for the scaffolding. As an example, in FIG. 5, the scaffolding contains loops, wherein each loop crosses on itself but is not attached at those points so the loops and the entire scaffolding may expand and contract.

Figure 6:
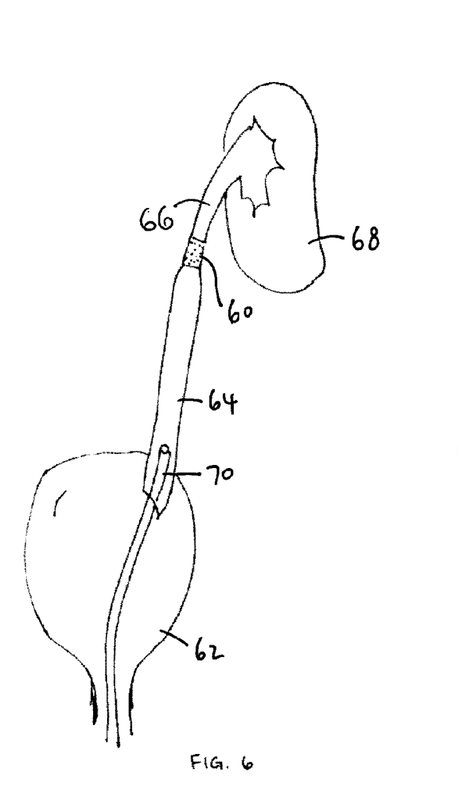
FIG. 6 is a perspective view of a ureter illustrating use of a plug to form a pressurized bladder and lower ureter below the plug and unpressurized upper ureter and kidney in accordance with one or more embodiments of the invention.

FIG. 6 illustrates compartmentalized pressurization in accordance with one or more embodiments of the invention. A plug 60 is used to form a pressurized bladder 62 and lower ureter 64 below the plug 60, and an unpressurized upper ureter 66 and kidney 68. The ureter portion 64 below the plug 60 is larger than the ureter portion 66 above the plug 60. The pressurization allows for slight dilation and opening of the ureter folds. This allows the scope 70 to have good visualization and allow for ureteroscopic work in the lower ureter 64, while protecting the kidney 68 from potentially harmful over-pressurization of the kidney 68 which could force water into the bloodstream or reduce the core body temperature. Although portions below the plug 60 are dilated, the pressurization may actually help keep the plug 60 in place. Potentially the pressure could even squeeze the gel axially, forcing the gel to expand radially and tightly against the lumen wall.

Figure 7:
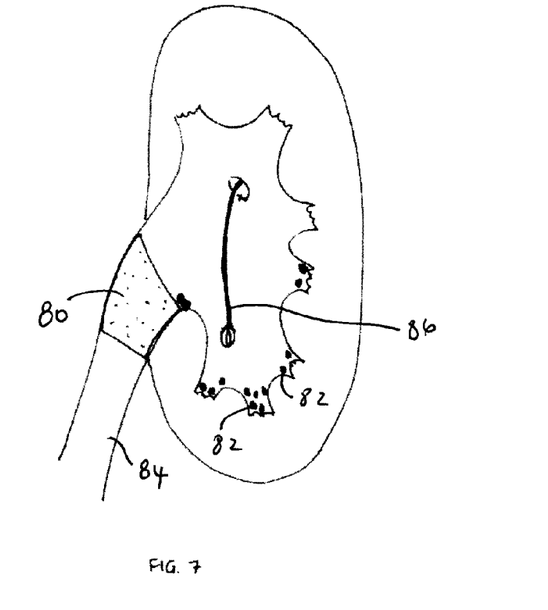
FIG. 7 is a perspective view of a ureter illustrating a percutaneous stone removal procedure with the ureter plugged in accordance with one or more embodiments of the invention.

FIG. 7 demonstrates how a plug 80 at the uretero-pelvic junction can prevent kidney stones 82 from traversing down the ureter 84, and potentially getting lodged, so that they may be extracted with a basket or other tool 86 percutaneously.

Figure 8:
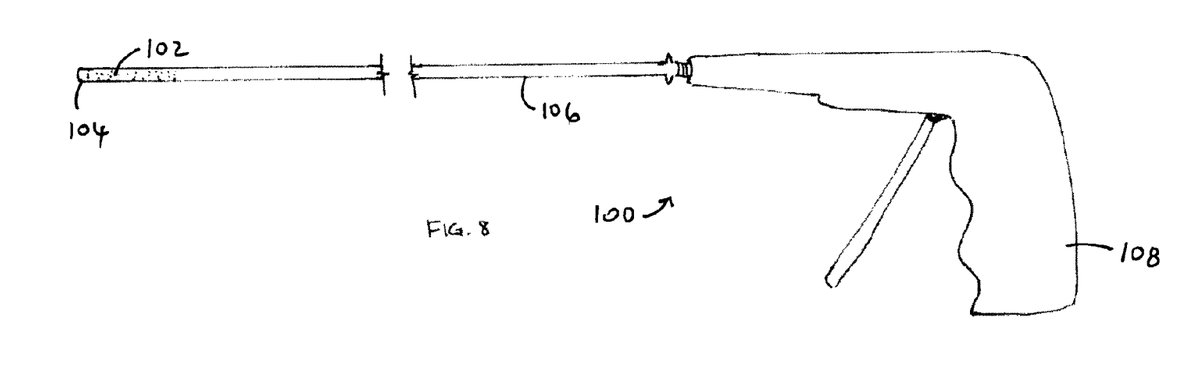
FIG. 8 is a side view of a delivery system in accordance with one or more embodiments of the invention.

FIG. 8 illustrates a delivery tool 100 with preloaded gel 102 at the catheter tip 104 in accordance with one a more embodiments of the invention. The delivery tool can include a catheter or tube 106 that is threaded onto a handle 108 so they may be separately sterilized and assembled at the time of delivery, as well as provide for a secure attachment under great force. However, snap-fit, hooks, slides, buckles and other common securing devices may also be used. A press-fit may also be suitable if so engineered to be secure under the strong force of the delivery. The handle 108 can utilize a full hand lever, so that a larger force may be applied than that of a standard syringe (or one finger), which may be necessary for a very viscous gel. A larger force may also be needed if a small catheter, such as 3 French, is to be used to deploy within a working channel of a flexible ureteroscope. The handle preferably allows for the delivery of the gel in one hand-crank for ease of use, although more may be used.

The handle 108 may deliver air, another liquid (such as, e.g., water), or a mechanical plunger as a pushing force. The handle 108 may have multiple ports to obtain or hold the pushing substance, or it may be preloaded.

The gel may be preloaded at the time of manufacture or pre-sterilization by artificially changing the temperature of the gel. For example, in a thermosensitive gel such as a Poloxamer, the gel can be refrigerated to 0° C. to force a liquid state (or heating it up for a bovine gelatin type), and then can be deployed through the system or can be drawn in from the tip proximally. In a non-liquid state, the material can be drawn in from the tip, e.g., by reversing the deployment mechanism, such as pulling on a syringe plunger.

Figure 9:
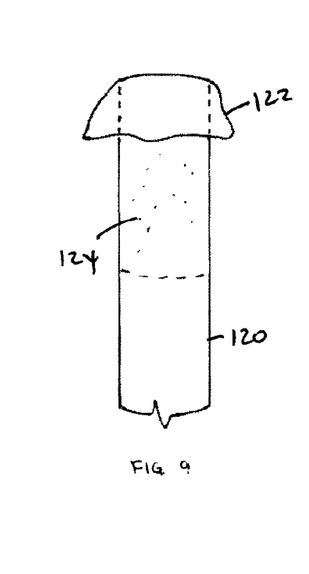
FIGS. 9-13 are perspective views of various catheter tips preloaded with a gel in accordance with one or more embodiments of the invention.

FIG. 9 is a detailed end view of a preloaded tip 120, with a peel-away wrapper 122 in accordance with one or more embodiments. The wrapper 122 is designed to contain the gel 124 inside the delivery system before use as well as protect the gel from contaminants. The wrapper 122 may adhere with an adhesive to the rim of the delivery tube. The wrapper 122 may utilize an additional or alternative securing method such as rubber band or tape, which would preferably all be discarded at the time of use. This end view also shows the gel 124 not fully filled to the very tip so that if the gel started to liquefy, it would have some room before being expelled.

Figure 10:
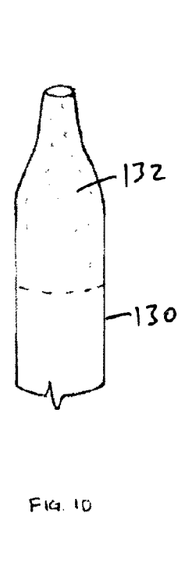

FIG. 10 is a detailed end view of a preloaded tip 130 with the tip tapered to a smaller diameter in accordance with one or more embodiments. The smaller diameter and therefore opening is so sized so that the viscosity of the gel 132 prevents the gel 132 from being expelled without external force applied on the opposite end, within a reasonable temperature range.

Figure 11:
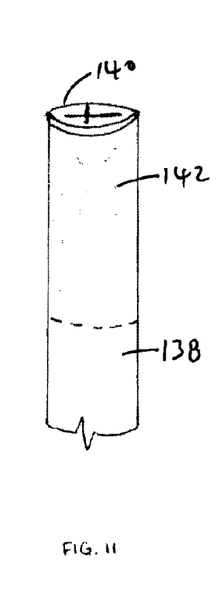

FIG. 11 depicts a detailed end view of a preloaded tip 138 that is capped with a flexible material 140, such as rubber or silicone in accordance with one or more embodiments. The cap 140 may have one or more slits, holes or other openings that are so sized so that the viscosity of the gel 142 prevents the gel 142 from being expelled without external force applied on the opposite end.

Figures 12, 13:
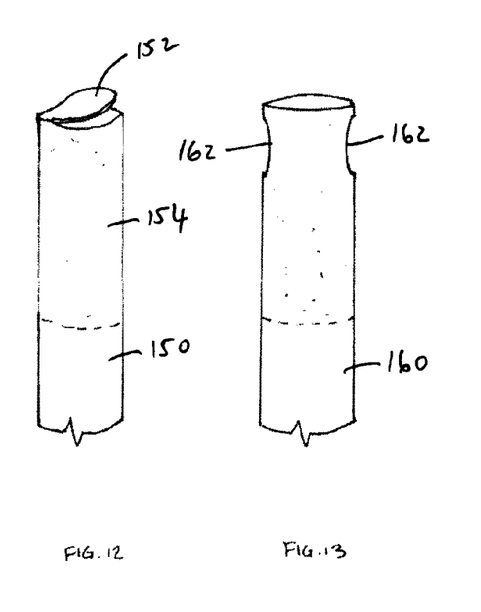

FIG. 12 depicts a detailed end view of a preloaded tip 150 that is capped with a flexible material 152 such as rubber or silicone in accordance with one or more embodiments. The cap 152 is secured on one side acting as a flap, where the natural, i.e., biased, position is closed. The strength of the hinge is determined so that the viscosity of the gel 154 keeps the gel 154 from being expelled without external force applied on the opposite end.

FIG. 13 depicts a detailed end view of a preloaded tip 160 with one or more openings 162 on the side of the catheter instead of the end axially in accordance with one or more embodiments. This allows the gel to be expelled generally radially, which may be advantageous to position the gel and allow it to adhere to the wall lining. The side openings 162 may be combined with any of the above mentioned embodiments to keep the gel from prematurely expelling. The side openings may be located in various strategic locations along the length of the tip 160.

Figures 14, 15, 16:
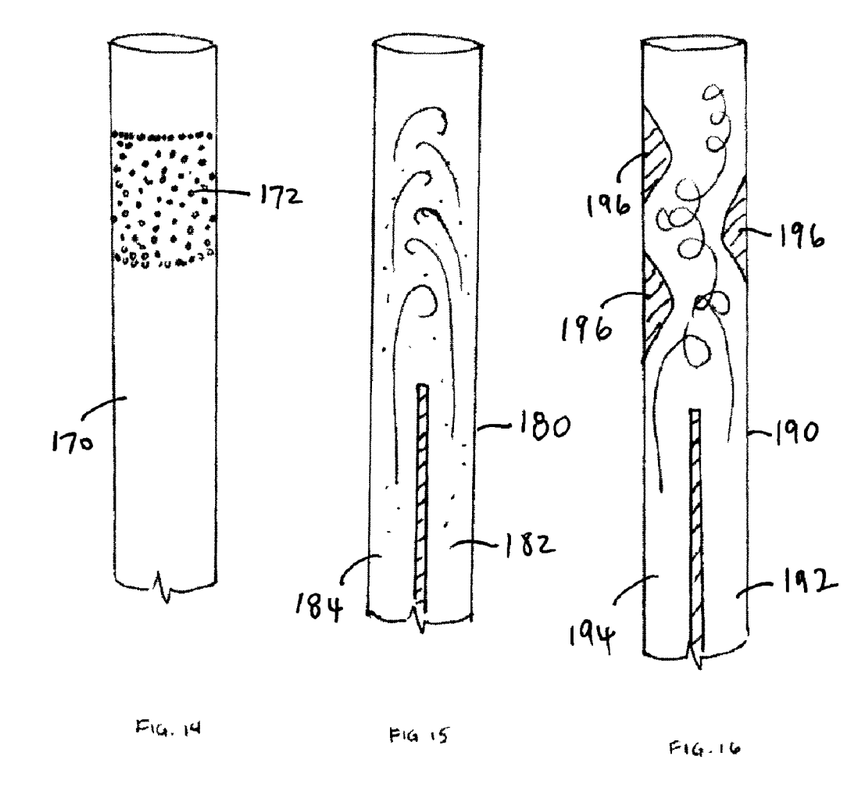
FIG. 14 is a perspective view of a catheter tip preloaded with a material that can be formed into a gel in accordance with one or more embodiments of the invention.
FIGS. 15 and 16 are perspective views of catheter tips of multi-lumen catheters in accordance with one or more embodiments of the invention.

FIG. 14 depicts a detailed end view of a preloaded tip 170 in accordance with one or more embodiments where the preloaded material 172 is a component of the final gel material. The material 172 shown in the figure is in a powder form. A liquid component may traverse the full length of the delivery system at the time of application to mix with the material 172. Alternatively, the material 172 may mix in the body with body fluid. When the two materials are mixed, the gel is formed and becomes viscous.

FIG. 15 depicts a detailed end view of a multi-lumen catheter 180 in accordance with one or more embodiments. The catheter 180 is used to deliver partial solutions or formulations in a more liquid state in separate passages 182, 184. The end portion has the partition removed so that the separate solutions may at least partially internally mix before being delivered.

FIG. 16 depicts a detailed end view of a multi-lumen catheter 190 in accordance with one or more embodiments. The catheter 190 is used to deliver partial solutions in a more liquid state in separate passages 192, 194. The end portion has the partition removed and has extra obstacles 196 to force a more turbulent flow and enhance mixing of the solutions.

In accordance with one or more embodiments of the invention, air is mixed into the thermosensitive polymer, giving it a foam appearance and texture. The air can be mixed into the thermosensitive polymer in the catheter or prior to introducing the thermosensitive polymer into the catheter. Use of foam can be advantageous because foam can traverse the catheter easier and it can better adhere to the body lumen wall.

Figures 17A, 17B:
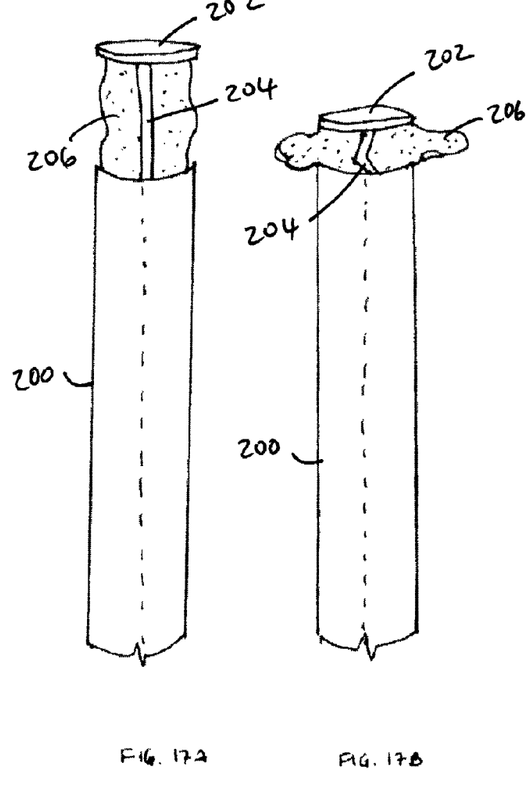
FIGS. 17A and 17B are perspective views of a catheter tip containing a movable end cap in accordance with one or more embodiments of the invention.

FIGS. 17A and 17B illustrate a catheter tip 200 and accordance with one or more embodiments of the invention. The catheter tip 200 includes a movable end cap 202. FIG. 17A shows the end cap 202 in a position significantly separated from the main catheter body. The end cap 202 is secured by an internal line 204, such as, e.g., a wire or suture, or externally with a movable, flexible material. The end cap 202 is then moved closer to the main catheter body, either by pulling on the internal line 204 or pushing the end cap onto an object such as a lumen wall. The movement of the end cap 202 then expels the gel 206. The gel sits in the end to be readily expelled generally radially as shown in FIG. 17B. Alternatively or additionally, the end cap 202 or internal line could have a plunger, pusher, inverted cone or other body that physically displaces the gel 206 at least partially sitting in the catheter body. It can be advantageous to force the gel material radially to better adhere to the lumen lining, fill a void, or be quicker to expel.

Figures 18, 19:
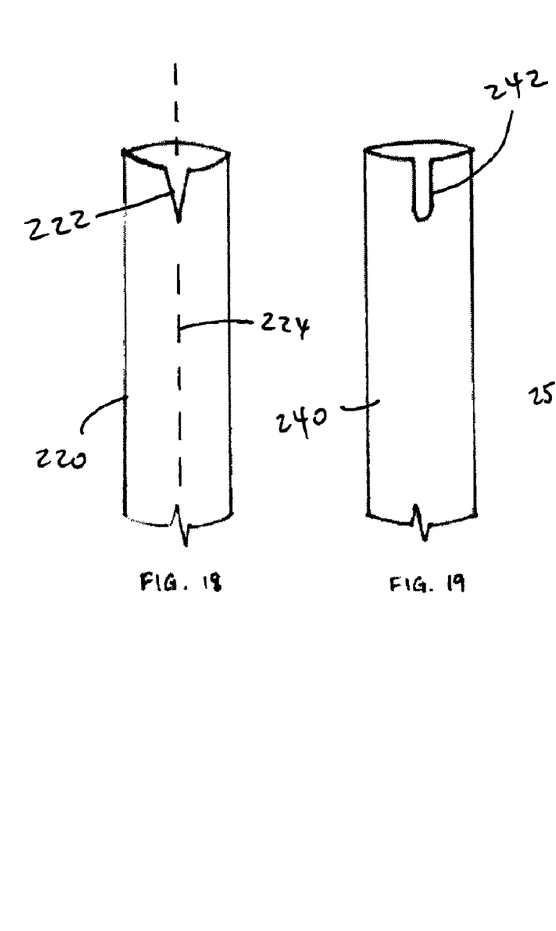

FIG. 18 depicts a detailed end view of a delivery catheter tip 220 in accordance with one or more embodiments of the invention. The catheter tip 220 includes an opening on the side of the catheter in the shape of a pointed slot or notch 222. This allows the gel to be expelled generally radially (i.e., in an outward direction from the central longitudinal axis 224 of the catheter tip), which improves positioning and adherence of the gel to the wall lining. The direction at which the gel will flow radially outward from the axis 224 through the opening 222 will vary depending on the speed of delivery, and may be, e.g., 45 degrees.

FIG. 19 depicts a detailed end view of a delivery catheter tip 240 in accordance with one or more embodiments of the invention. The catheter tip 240 includes an opening on the side of the catheter in the shape of a rounded slot 242, with the end being milled. The opening allows the gel to be expelled generally radially, which improves positioning and adherence of the gel to the wall lining.

Figures 20, 21A:
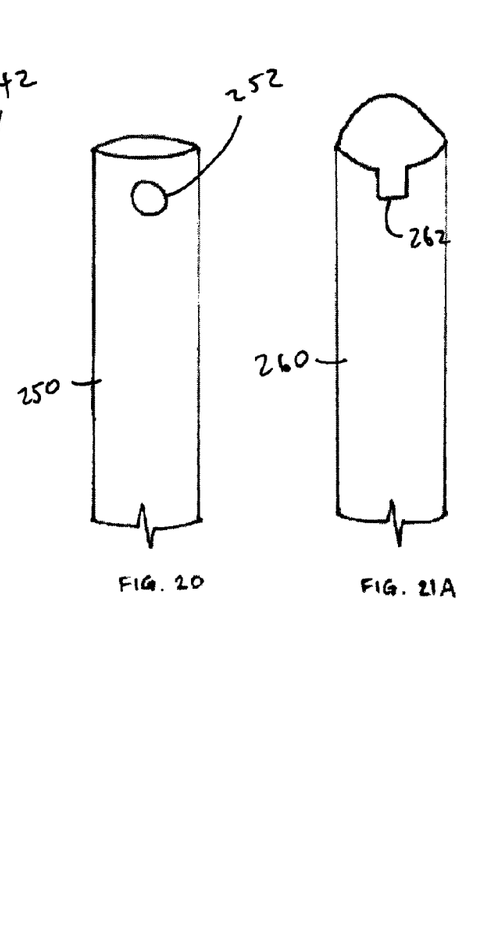

FIG. 20 depicts a detailed end view of a delivery catheter tip 250 in accordance with one or more embodiments of the invention. The catheter tip 250 includes an opening on the side of the catheter in the shape of a circle 252, the hole being drilled. The opening allows the gel to be expelled generally radially, which improves positioning and adherence of the gel to the wall lining.

Figure 21B:
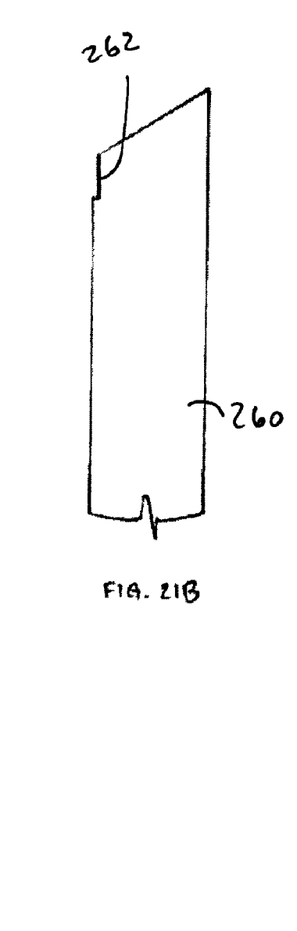

FIGS. 21A and 21B show front and side views, respectively, of a delivery catheter tip 260 in accordance with one or more embodiments of the invention. The catheter tip 260 includes an opening on a side of the catheter in the shape of a square slot 262. The opening allows the gel to be expelled generally radially, which improves positioning and adherence of the gel to the wall lining. The advancing edge of the catheter tip 260 is not perpendicular to the catheter axis, but includes a taper that helps further expel the gel radially while providing a guiding edge. The use of a tapered advancing edge can be incorporated in any of the catheter tips described herein.

Although only one side opening is shown in each of the FIGS. 18-21 drawings, it should be understood that multiple side opening can be incorporated in each of the catheter tips to further increase radial gel flow.

In each of the embodiments having side openings, the leading edge of the catheter tip can be closed (e.g., with an end cap or otherwise) such that gel is expelled only out of the side openings for radial gel flow.

The catheter tips shown in FIGS. 18-21 can be preloaded with gel as in the embodiments of FIGS. 9-13. Alternatively, the FIGS. 18-21 catheter tips can be part of a delivery tool like the tool shown in FIG. 8 wherein the gel traverses the entire length of the catheter before being deposited in the lumen.

In accordance with one or more embodiments of the invention, the catheter tip is rotated or twisted while gel is being expelled radially from the tip, thereby rotating the side opening(s) on the tip, so that gel is expelled around the catheter. Consequently, as the catheter is slowly withdrawn, the gel more completely fills space in the lumen.

Having described preferred embodiments of the present invention, it should be apparent that modifications can be made without departing from the spirit and scope of the invention.

The invention claimed is:

1. A method for temporarily occluding a body opening, comprising the steps of:
    introducing a tip of a catheter into the body opening, the tip including a central longitudinal axis;
    advancing a pre-mixed thermosensitive polymer through substantially the length of a single lumen of the catheter and expelling the thermosensitive polymer from the tip of the catheter into a portion of the body opening, with at least a portion of the thermosensitive polymer being expelled from the tip in a direction generally radially outward from the central longitudinal axis to promote adherence of the thermosensitive polymer on a wall defining the body opening;
    at least partially withdrawing the tip from the body opening and allowing the thermosensitive polymer to harden as it warms to body temperature to form a plug in the body opening; and
    removing said plug by a subsequent cooling of said thermosensitive polymer wherein removing said plug comprises applying a cool liquid to said thermosensitive polymer.

2. The method of claim 1 wherein the thermosensitive polymer comprises a mixture of Poloxamers 338, 407, 237, or 188, or some combination thereof, and water.

3. The method of claim 1 wherein temporarily occluding a body opening includes temporarily occluding a body lumen.

4. The method of claim 1 wherein temporarily occluding a body opening includes temporarily filling a body cavity.

5. The method of claim 1 wherein temporarily occluding a body opening includes temporarily occluding a hole in the body.

6. The method of claim 1 wherein the step of introducing a tip of a catheter into the body opening comprises introducing a tip of an insulated catheter into the body opening.

7. The method of claim 6 wherein said insulated catheter comprises an insulator material selected from the group consisting of polyimide, polyolefin, polyether block amides, and polyester.

8. The method of claim 1 wherein said cool liquid comprises chilled water.

9. The method of claim 1 wherein applying said cool liquid comprises applying said cool liquid to an external surface of said thermosensitive polymer.

10. A method for temporarily occluding a body opening, comprising the steps of:
    introducing a tip of a catheter into the body opening, the tip including a central longitudinal axis;
    advancing a pre-mixed thermosensitive polymer through substantially the length of a single lumen of the catheter and expelling the thermosensitive polymer from the tip of the catheter into a portion of the body opening;
    at least partially withdrawing the tip and allowing the thermosensitive polymer to harden as it warms to body temperature to form a plug in the body opening; and removing said plug by applying a cool material to said thermosensitive polymer through a catheter.

11. The method of claim 10 wherein applying said cool material comprises poking an external surface of said thermosensitive polymer and applying a chilled liquid within said polymer.

12. The method of claim 11 wherein said poking comprises puncturing said external surface of said thermosensitive polymer with said tip of said catheter.

13. The method of claim 11 wherein said poking comprises puncturing said external surface of said thermosensitive polymer with a tip of a guide wire, a portion of said guide wire being disposed within said catheter.

14. The method of claim 13 wherein said guide wire comprises a hollow wire.

15. The method of claim 13 wherein said portion of said guide wire is disposed within said single lumen of said catheter.

16. A method of temporarily occluding a body opening as defined in claim 10 wherein said applying a cool material to said thermosensitive polymer comprises applying a chilled liquid to said thermosensitive polymer.

17. A method of temporarily occluding a body opening as defined in claim 16 wherein said chilled liquid comprises chilled water.

18. The method of claim 10 wherein applying said cool material comprises applying said cool material to an external surface of said thermosensitive polymer.

19. The method of claim 10 wherein the thermosensitive polymer comprises a mixture of Poloxamers 338, 407, 237, or 188, or some combination thereof, and water.

20. The method of claim 10 wherein temporarily occluding a body opening includes temporarily occluding a body lumen.

21. The method of claim 10 wherein temporarily occluding a body opening includes temporarily filling a body cavity.

22. The method of claim 10 wherein temporarily occluding a body opening includes temporarily occluding a hole in the body.

23. The method of claim 10 wherein the step of introducing a tip of a catheter into the body opening comprises introducing a tip of an insulated catheter into the body opening.

24. A method for temporarily occluding a body opening, comprising the steps of:
    introducing a tip of a catheter into the body opening, the tip including a central longitudinal axis;
    advancing a pre-mixed thermosensitive polymer through substantially the length of a single lumen of the catheter and expelling the thermosensitive polymer from the tip of the catheter into a portion of the body opening, with at least a portion of the thermosensitive polymer being expelled from the tip in a direction generally radially outward from the central longitudinal axis to promote adherence of the thermosensitive polymer on a wall defining the body opening;
    at least partially withdrawing the tip from the body opening and allowing the thermosensitive polymer to harden as it warms to body temperature to form a plug in the body opening; and
    removing said plug by a subsequent cooling of said thermosensitive polymer wherein removing said plug comprises applying a cryoprobe to said thermosensitive polymer.

* * * * *